(12) United States Patent
Ravindran

(10) Patent No.: US 8,457,723 B2
(45) Date of Patent: *Jun. 4, 2013

(54) HEART RATE DETECTION IN HIGH NOISE CONDITIONS

(75) Inventor: Sourabh Ravindran, Dallas, TX (US)

(73) Assignee: Texas Instruments Incorporated, Dallas, TX (US)

(*) Notice: Subject to any disclaimer, the term of this patent is extended or adjusted under 35 U.S.C. 154(b) by 570 days.

This patent is subject to a terminal disclaimer.

(21) Appl. No.: 12/572,198

(22) Filed: Oct. 1, 2009

(65) Prior Publication Data

US 2010/0094150 A1 Apr. 15, 2010

Related U.S. Application Data

(60) Provisional application No. 61/104,030, filed on Oct. 9, 2008.

(51) Int. Cl.
*A61B 5/0402* (2006.01)

(52) U.S. Cl.
USPC ........................................ 600/509

(58) Field of Classification Search
USPC ................................ 600/508–525
See application file for complete search history.

(56) References Cited

PUBLICATIONS

"Multi-component based cross correlation beat detection in electrocardiogram analysis"; Biomed Eng Online V.3; 2004; Thorsten Last, Chris D Nugent and Frank J Owens. Referred to herein as Last.*
Lawrence R. Rabiner, "On the Use of Autocorrelation Analysis for Pitch Detection", IEEE Transactions on Acoustics, Speech, and Signal Processing, vol. ASSP-25, No. 1, Feb. 1977, pp. 24-33.
Chris Peters, et al., "Heart Rate Detection in Low Amplitude Non-Invasive Fetal ECG Recordings," Proceedings of the 28th IEEE EMBS Annual International Conference, New York City, New York, Aug. 30-Sep. 3, 2006, pp. 6092-6094.
Jung H. Lee, et al., "Fast Cross-Correlation Method for Real Time Detection of Fetal Heart Rate," Proceedings of the 20th Annual International Conference of the IEEE Engineering in Medicine and Biology Society, vol. 20, No. 1, 1998, pp. 178-181.
Sourabh Ravindran, et al., "Real-Time, Low-Complexity, Low-Memory Solution to ECG-Based Heart Rate Detection," presented at the IEEE Engineering in Medicine and Biology Conference, Sep. 3, 2009, pp. 1-4.

* cited by examiner

*Primary Examiner* — Carl H Layno
*Assistant Examiner* — Paula J Stice
(74) *Attorney, Agent, or Firm* — Mirna Abyad; W. James Brady; Frederick J. Telecky, Jr.

(57) ABSTRACT

A method of processing heart monitoring samples is provided that includes computing a folded correlation value for each heart monitoring sample in a plurality of heart monitoring samples and identifying peaks corresponding to heartbeats based on the folded correlation values of the heart monitoring samples.

14 Claims, 6 Drawing Sheets

HEART RATE DETECTION IN HIGH NOISE CONDITIONS

CLAIM OF PRIORITY UNDER 35 U.S.C. 119(e)

The present application claims priority to U.S. Provisional Patent Application No. 61/104,030, filed on Oct. 9, 2008, entitled "Folded Correlation Based Method for Primary Heart Sound Location Detection in the Presence of Very High Noise Background" which is incorporated by reference herein.

BACKGROUND OF THE INVENTION

Accuracy of heart rate detection is important in many commercial heart monitoring applications (e.g., heart rate monitors in exercise equipment, personal heart rate monitors, etc.) and medical heart monitoring applications (e.g., digital stethoscopes, mobile cardiac monitoring devices, etc.). Background environmental noise such as music, wind, television, traffic, voices, vibrations, body movements, etc., can introduce noise into signals received by the sensors (or other signal capture components) used in heart monitoring applications and adversely affect the accuracy of the heart rate detection. Accordingly, methods for robust heart rate detection in high noise conditions are desirable.

BRIEF DESCRIPTION OF THE DRAWINGS

Particular embodiments in accordance with the invention will now be described, by way of example only, and with reference to the accompanying drawings.

DETAILED DESCRIPTION OF EMBODIMENTS OF THE INVENTION

Figure 1:
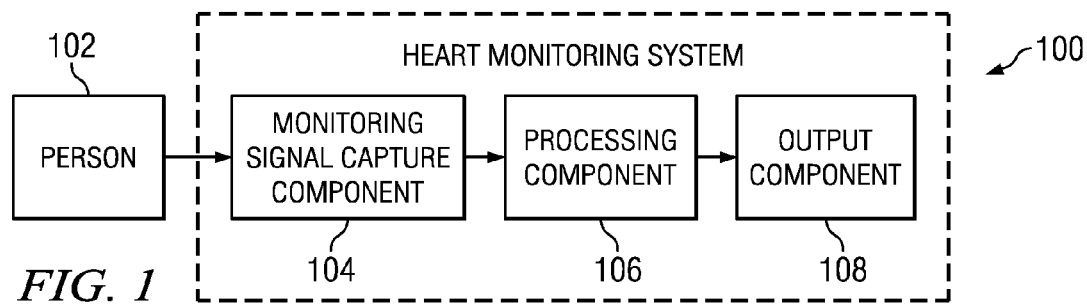
FIGS. 1 and 2 show digital systems in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description. In addition, although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

Certain terms are used throughout the following description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" and derivatives thereof are intended to mean an indirect, direct, optical, and/or wireless electrical connection. Thus, if a first component couples to a second component, that connection may be through a direct electrical connection, through an indirect electrical connection via other devices and connections, through an optical electrical connection, and/or through a wireless electrical connection.

In general, embodiments of the invention provide for processing of heart monitoring samples to identify peaks corresponding to heartbeats, i.e., cardiac cycles. The processing performed provides improved identification of these peaks in the presence of high background noise by generating a folded correlation value for the heart monitoring samples and identifying the peaks based on the folded correlation values. Further, in some embodiments of the invention, the identified peaks are used to determine the heart rate, e.g., the heart rate may be determined based on the number of peaks and the sampling frequency. In some embodiments, the heart rate is displayed. In addition, in some embodiments of the invention, an annotated graphical representation of the heart monitoring samples (e.g., a phonocardiograph) that shows the locations of the identified peaks may be displayed.

Figure 2:
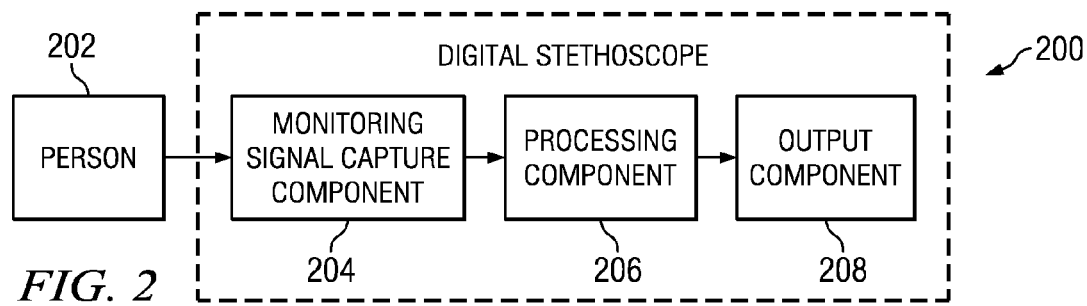

FIGS. 1 and 2 show digital systems for heart monitoring in accordance with one or more embodiments of the invention. The digital system of FIG. 1 is a heart monitoring system (100) that includes a monitoring signal capture component (104), a processing component (106), and an output component (108). While each of these components is depicted and described separately, one of ordinary skill in the art will know that any two or all three of the components may be combined in a single digital system. The monitoring signal capture component (104) is configured to capture a heart monitoring signal from a person (102) and provide the captured heart monitoring signal to the processing component (106). In various embodiments, the heart monitoring signal may be provided to the processing component (106) in real-time, may be provided periodically as the signal is being captured, and/or may be recorded and provided to the processing component (106) at a later time.

The monitoring signal capture component (104) includes a monitoring signal sensor (not specifically shown) that captures analog signals from the heart of a person (102). The monitoring signal sensor may be any suitable sensor, such as, for example, an audio (i.e., sound) sensor, an accelerometer, or two or more electrocardiogram (ECG) electrodes. The analog signals may be, for example, sound waves of the person's (102) heart sounds, vibrations from motion caused by contraction and relaxation of the person's (102) heart, or electrical signals from two or more places on the person's (102) body. Further, the monitoring signal sensor is placed in sufficient proximity to the person (102) to sense the desired heart monitoring signals. For example, the monitoring signal sensor may be attached to the person's (102) skin, surgically implanted in the person's body (102), worn by the person (102) (e.g., a necklace, watch, wrist band, chest band, etc.), or incorporated into exercise equipment.

The monitoring signal capture component (104) may include functionality to convert the analog heart monitoring signals to digital signals of heart monitoring samples, e.g., an analog to digital converter. In some embodiments of the invention, monitoring signal capture component (104) may include functionality to amplify the digital signal and/or perform other optimizations (e.g., noise reduction) on the digital signal before providing the signal to the processing component (106). While the remainder of this description assumes that the analog heart monitoring signals are converted to digital signals prior to transmission of the signals to the processing component (106), one of ordinary skill in the art will understand embodiments of the invention in which the analog signals are transmitted and subsequently converted to digital signals by the processing component (106).

The digital heart monitoring signal may be provided to the processing component (106) by wired or wireless forms of communication. More specifically, the monitoring signal capture component (104) may be directly connected to the processing component (106) (e.g., using a USB port, electrode wires, logic circuitry, etc.) or may be indirectly connected to the processing component (106) by, for example, a network (not specifically shown), a Bluetooth connection, etc. The network may be a wide area network (WAN) such as the Internet, a wireless network, a local area network (LAN), or a combination of networks.

The processing component (106) may be any suitable digital system (e.g., a general purpose processor, a digital processor, a personal heart rate monitoring system, a hear rate monitoring system in a piece of exercise equipment, a personal computer, a laptop computer, a server, a mainframe, a personal digital assistant, a television, a cellular telephone, an iPod, an MP3 player, etc.) configured to receive the digital heart monitoring signal from the monitoring signal capture component (104). The processing component (106) is configured to process the digital heart monitoring samples in the digital heart monitoring signal in accordance with embodiments of methods described herein. In one or more embodiments of the invention, the processing component (106) includes functionality, e.g., a computer readable medium such as memory, a flash memory, an optical storage device, a disk drive, etc., to store executable instructions implementing an embodiment of a method for processing heart monitoring samples as described herein and to execute those instructions.

In some embodiments of the invention, the processing component (106) is configured to provide a heart rate computed in accordance with embodiments of methods described herein to the output component (108) for display. In some embodiments of the invention, the processing component (106) is configured to generate a graphical representation of the digital heart monitoring signal, e.g., a phonocardiogram (PCG) or other waveform, to the output component (108) for display. The graphical representation may be annotated to show the locations of peaks corresponding to the heartbeats that are identified by the heart monitoring sample processing method.

The transmission of data from the processing component (106) to the output component (108) may be wired or wireless. More specifically, the output component (108) may be directly connected to the processing component (106) (e.g., using a USB port, a controller card, control circuitry, etc.) or may be indirectly connected to the processing component (104) by a network (not specifically shown), a Bluetooth connection, etc. The network may be a wide area network (WAN) such as the Internet, a wireless network, a local area network (LAN), or a combination of networks. The output component (106) may be any suitable display device such as, for example, a computer monitor, a display of a handheld computing device, a display in a personal heart rate monitoring device, a display in a piece of exercise equipment, etc. The output component (106) may also be another digital system that includes a display device.

FIG. 2 shows a digital stethoscope (200) configured to process heart monitoring samples in accordance with embodiments of methods described herein. The digital stethoscope (200) includes a monitoring signal capture component (204), a processing component (206), and an output component (208). The digital stethoscope (200) also includes speakers (not specifically shown). The monitoring signal capture component (204) is configured to capture heart sounds, i.e., a heart monitoring signal, from a person (202) and provide the captured heart sounds to the processing component (206) as an audio signal. The monitoring signal capture component (204) may be circuitry in a chest piece of the digital stethoscope (200) and/or in the body of the digital stethoscope (200). More specifically, the monitoring signal capture component (204) may include functionality to convert the sound waves of the person's (202) heart sounds to a digital audio signal of heart monitoring samples that is provided to the processing component (206) continuously (e.g., by direct audio output) as the heart sounds are captured. In some embodiments of the invention, the monitoring signal capture component (204) may include functionality to amplify the digital audio signal and/or perform other optimizations (e.g., noise reduction) on the digital audio signal before providing the signal to the processing component (206).

The processing component (206) is one or more processors configured to receive the digital audio signal from the monitoring signal capture component (204). For example, the processing device may be a digital signal processor (DSP), a microprocessor, or a combination of a DSP and a microprocessor. The processing component (206) is configured to process the digital heart monitoring samples in the digital audio signal in accordance with embodiments of methods described herein. In one or more embodiments of the invention, the processing component (206) includes functionality, e.g., a computer readable medium such as memory, a flash memory, an optical storage device, a disk drive, etc., to store executable instructions implementing an embodiment of a method for processing heart monitoring samples as described herein and to execute those instructions.

In some embodiments of the invention, the processing component (206) is configured to provide a heart rate computed in accordance with embodiments of methods described herein to the output component (208) for display. In some embodiments of the invention, the processing component (206) is configured to generate a graphical representation of the digital heart monitoring signal, e.g., a phonocardiogram (PCG), and provide the graphical representation to the output component (108) for display. The graphical representation may be annotated to show the locations of peaks corresponding to the heartbeats that are identified by the heart monitoring sample processing method.

The output component (208) is a display included in the body of the digital stethoscope (200) and operatively connected to the processing component (206) by control circuitry. Further, the output component (208) is configured to receive the heart rate and/or graphical representation from the processing component (206) and to display the heart rate and/or graphical representation.

Figure 3:
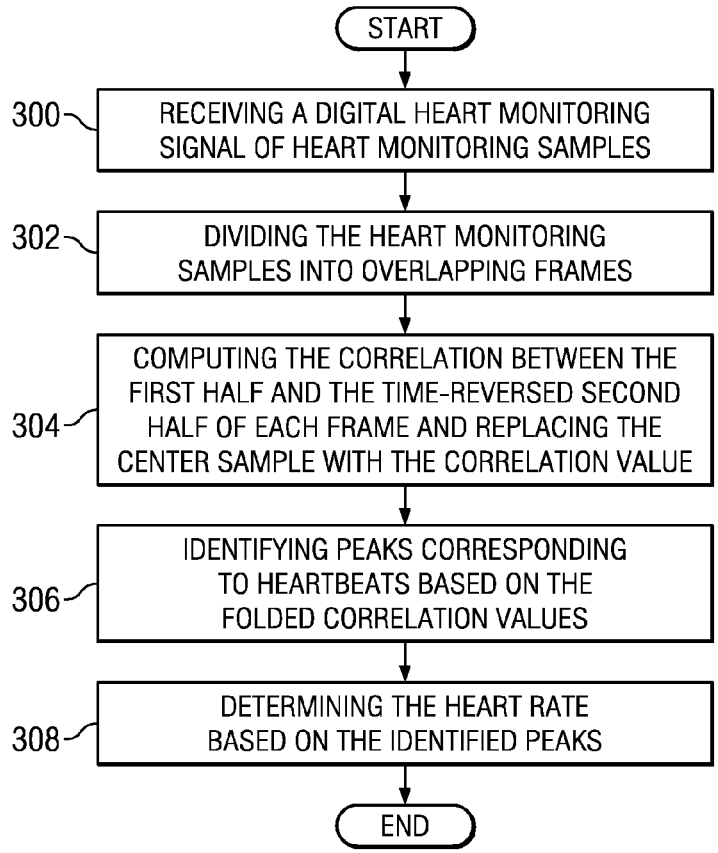
FIG. 3 shows a flow diagram of a method for processing heart monitoring samples in accordance with one or more embodiments of the invention.

FIG. 3 is a flow diagram of a method for processing heart monitoring samples in accordance with one or more embodiments of the invention. Initially, a digital heart monitoring signal of heart monitoring samples is received (300). The digital signal is generated by converting an analog heart monitoring signal to the digital signal. The digital signal may be received in real-time, periodically, or may be pre-recorded.

In some embodiments of the invention, the digital heart monitoring signal is of sufficient length to represent at least three cardiac cycles, i.e., heartbeats. The frequency of the cardiac cycles, i.e., the number of times a cardiac cycle occurs in some time period, is the heart rate. As is explained in more detail below, the frequency of the cardiac cycles can be determined by identifying certain peaks in the heart monitoring samples.

The analog heart monitoring signal may be an audio signal of heart sounds or a voltage signal representing electrical activity of the heart. More specifically, if the analog heart monitoring signal is captured by an audio sensor or accelerometer, the signal is a multi-component signal of heart sounds that includes, among other components, primary heart sound components. The primary heart sound components, S1 and S2, are composite acoustic signals generated by valve closures (i.e., S1 is caused by the closure of the mitral and tricuspid values and S2 is caused by the closing of the aortic and pulmonary valves). If the analog heart monitoring signal is captured by two or more ECG electrodes, the signal is voltage representing electrical activity of the heart, i.e., the signal generated in a person's body to cause the heart to contract or relax. This signal has three main components, a P-wave, a QRS complex made up of a Q-wave, an R-wave, and an S-wave, and a T-wave. The P-wave represents the depolarization (electrical activation) of the atria of the heart. The QRS complex represents the ventricular activity of the heart. The T-wave represents the repolarization of the ventricles.

Referring again to FIG. 3, the digital heart monitoring samples are divided into overlapping frames (302). More specifically, the heart monitoring samples are divided into frames of N samples that overlap by N-1 samples. The value of N is an odd number and is selected depending on the signal being processed and the sampling rate. In general, the value of N is selected to be approximately the width of a desired signal event (e.g., an S1, S2, or R-wave). For example, S1 is typically about 100-150 milliseconds long. If the sampling frequency is 1000 Hertz, N may be an odd number between 101 and 151. In some embodiments of the invention, the value of N may be selected by the user of a digital system incorporating the method. In some embodiments of the invention, the value of N may be set to a default value based on the type of signal to be processed, i.e., the type of sensor to be used to capture signals from the heart.

The heart monitoring samples in each frame are then folded around the center heart monitoring sample in the frame to generate a folded correlation value for the center sample (304). More specifically, a dot product of a vector of the samples in a frame preceding the center sample in time and a vector of the samples in the frame following the center sample in time is computed to generate the folded correlation value of the center sample. The samples in the former vector are in time order and the samples in the latter vector are in reverse time order. For example, assume a frame includes seven samples, s1, s2, s3, s4, s5, s6, and s7, in which s1 is the earliest sample in time and s7 is the latest sample in time. The folded correlation value of the center sample s4 is the dot product of a vector [s1, s2, s3] and a vector [s7, s6, s5], i.e., (s1*s7)+(s2*s6)+(s3*s5). The center sample, s4, is replaced by the folded correlation value. Note that this process is similar to a zero lag cross-correlation between the first half of the frame and a time-reverse second half of the frame. Further, this process may be viewed as replacing each sample in the heart monitoring samples between the first (N-1)/2 samples and the last (N-1)/2 samples with the cross correlation between the (N-1)/2 samples before the sample and the time-reversed (N-1)/2 samples after it. Note that samples around desired signal events (e.g., an S1, S2, or R-wave) should produce a larger folded correlation value than background noise as these desired signal events likely have more symmetry around their peaks than the background noise.

In some embodiments of the invention, steps 302 and 304 may be applied recursively. That is, for each recursion, the correlated digital heart monitoring samples resulting from these steps in the previous recursion are divided into overlapping frames (with perhaps a different frame size) and new correlations computed as described above. Each recursion would enhance the peaks more, thus making identification of the desired peaks easier. Such recursive application may be desirable, for example, for heart monitoring signals captured in the presence of extremely high noise.

Peaks corresponding to heartbeats, i.e., peaks corresponding to the desired signal events, are then identified based on the folded correlation values (306). For example, if the digital heart monitoring signals represent heart sounds, S1 peaks and S2 peaks are identified. And, if the digital heart monitoring signals represent electrical activity of the heart, R-wave peaks are identified. Techniques for identifying these types of peaks are well-known in the art and any suitable technique may be used.

The heart rate is then determined based on the identified peaks (308). If the identified peaks are S1 peaks, the heart rate may be determined based on the number of S1 peaks identified and the sampling frequency of the signal. For example, if $L_s$ is the number of S1 peaks, $F_s$ is the sampling frequency, x is the location of the first S1 peak in the heart monitoring samples, and y is the location of the last S1 peak in the heart monitoring samples, then the heart rate is equal to $((L_s-1)*60*F_s)/(y-x)$ beats per minute (BPM). If the identified peaks are R-wave peaks, the heart rate may be determined based on the number of R-wave peaks identified and the sampling frequency of the signal.

In some embodiments of the invention, the heart rate is displayed on a display device. The heart rate may also be updated as additional heart monitoring samples are processed. In some embodiments of the invention, the heart rate may be stored periodically to generate a history of heart rates. In some embodiments of the invention, a waveform of the heart monitoring samples may also be generated and displayed. The locations of the identified S1 and S2 peaks, or R-wave peaks may demarcated, i.e., annotated, in the waveform using symbols, colors, and/or any other suitable demarcation scheme.

FIGS. 4-7 show example phonocardiograms (PCGs) of the results of applying an implementation of an embodiment of a method of processing heart monitoring samples described herein to sample audio signals of heart sounds. These figures illustrate the ability of the method to distinguish the primary heart sounds, S1 and S2, from background noise.

Figure 4:
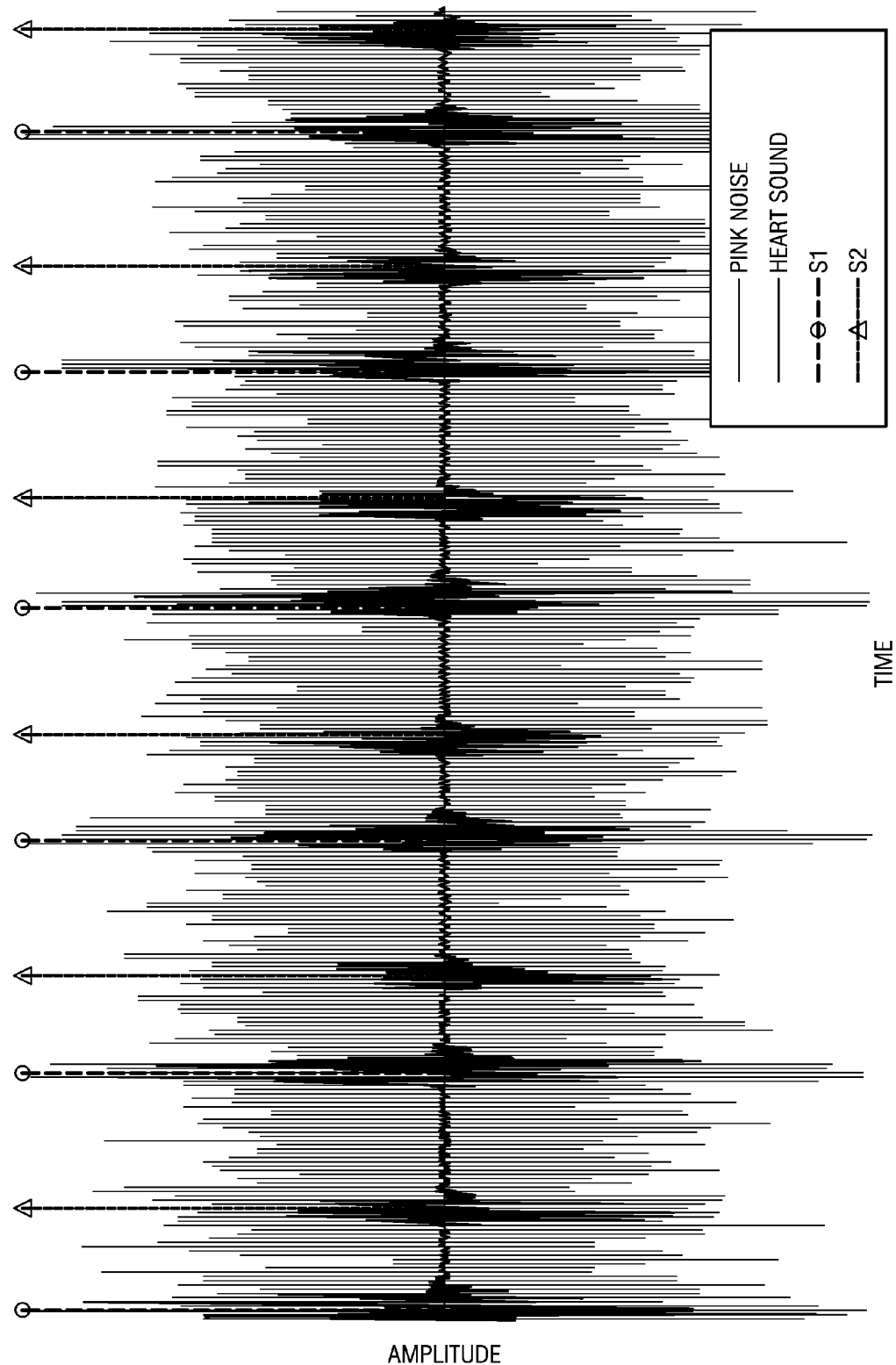
FIGS. 4-7 show graphs of test results in accordance with one or more embodiments of the invention.
Figure 5:
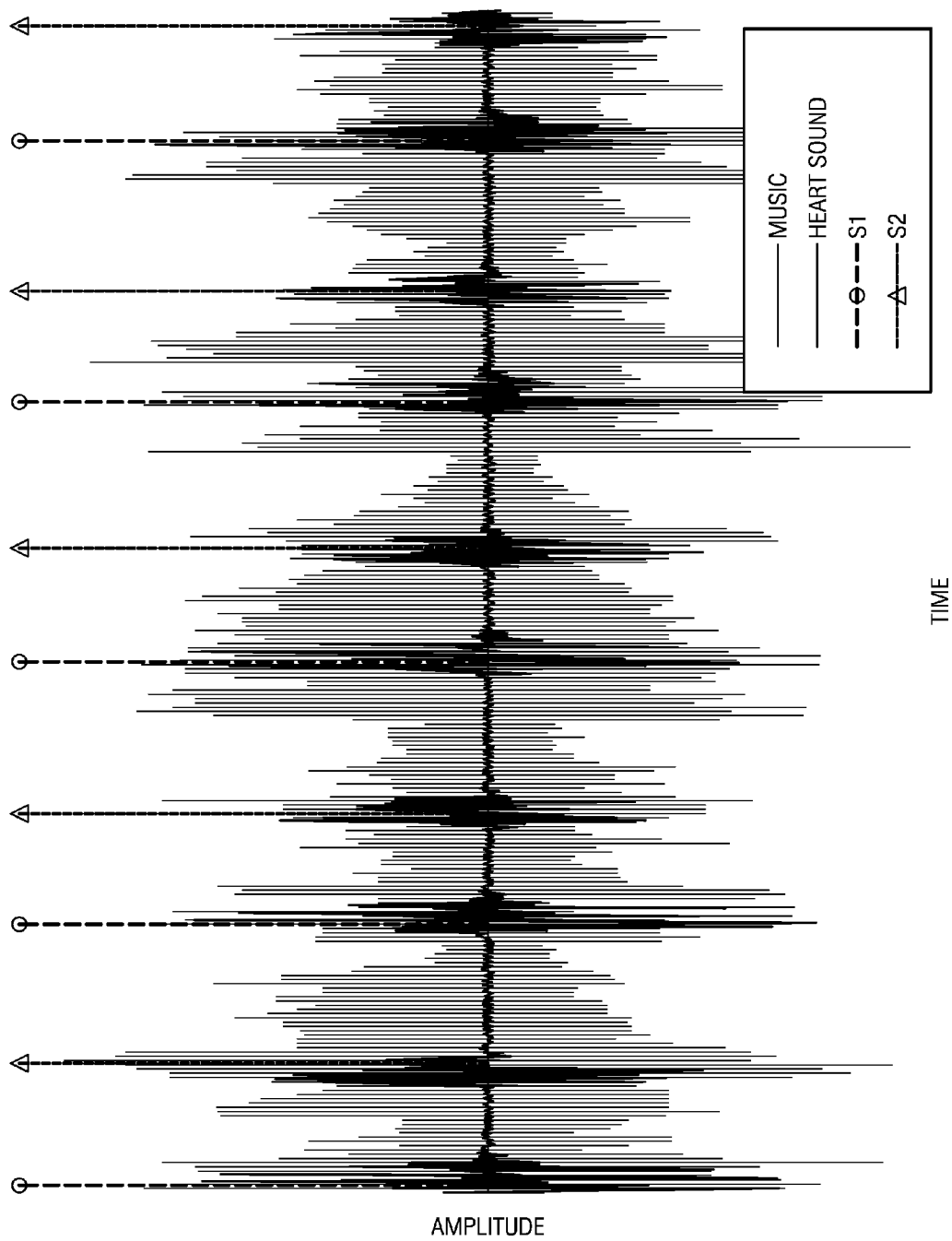
Figure 6:
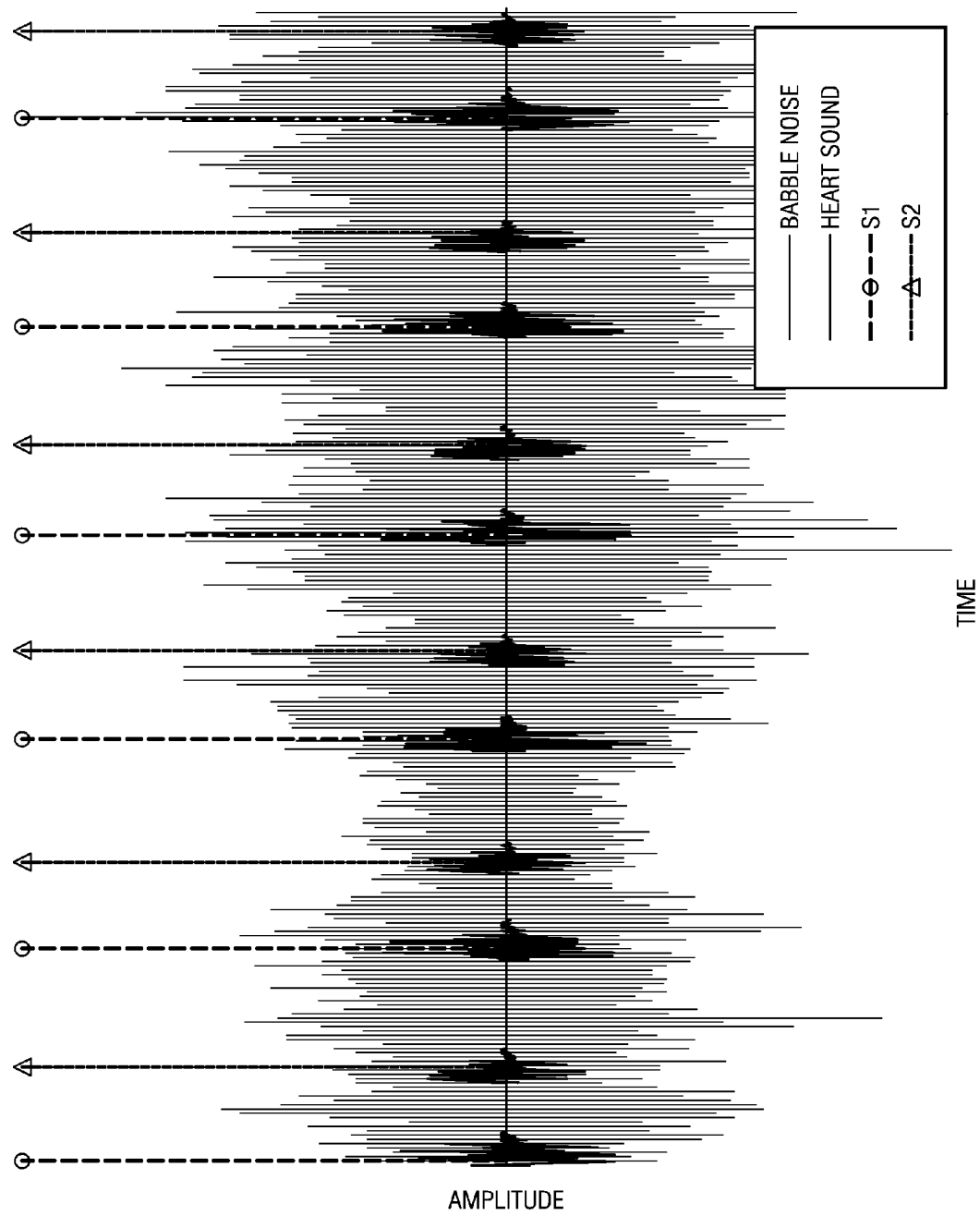
Figure 7:
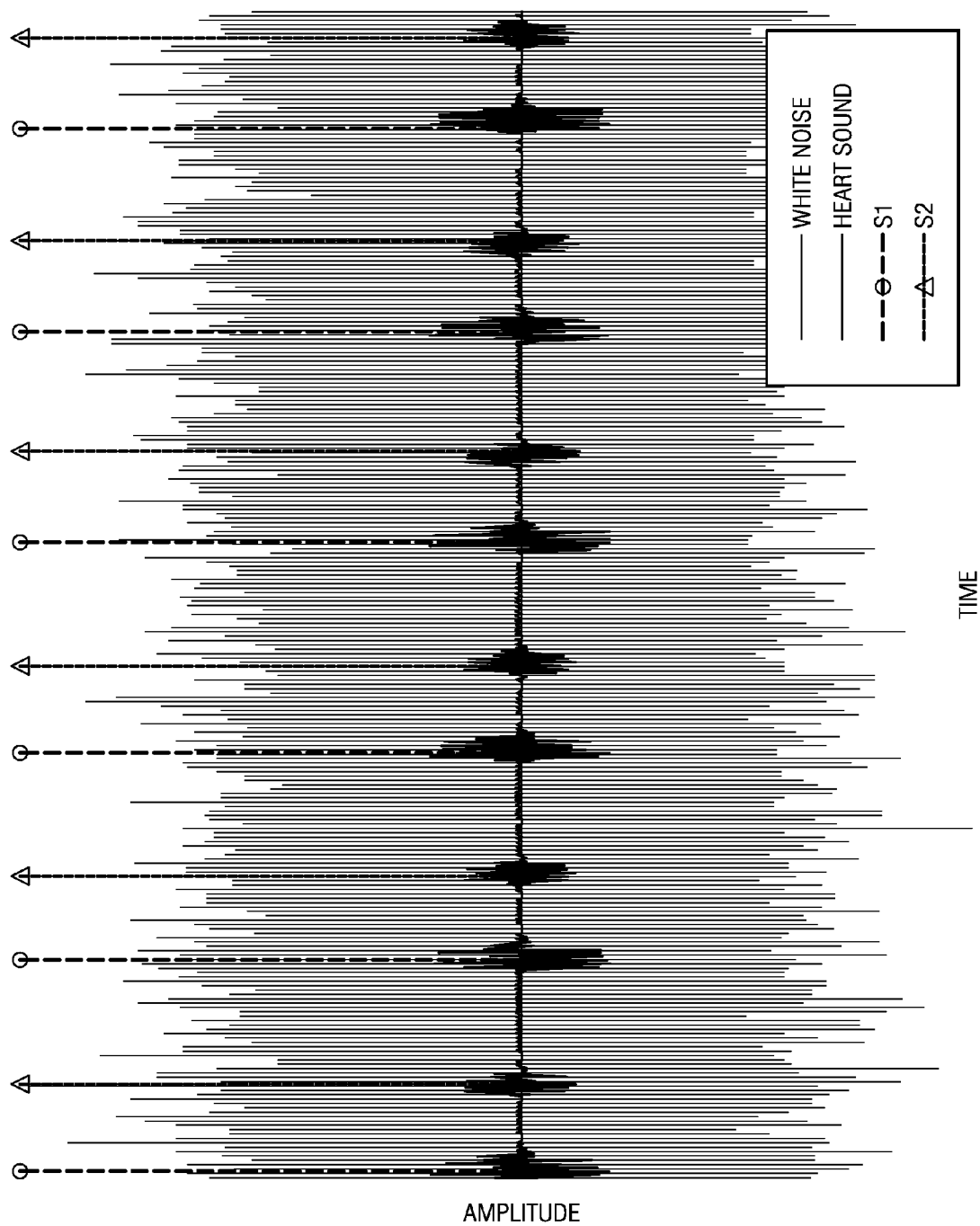

FIG. 4 shows the results in the presence of synthetically added pink noise at 0 dB SNR. FIG. 5 shows the results in the presence of synthetically added music at 0 dB SNR. FIG. 6 shows the results in the presence of synthetically added babble noise at −10 dB SNR. FIG. 7 shows the results in the presence of synthetically added white noise at −15 dB SNR.

Figure 8:
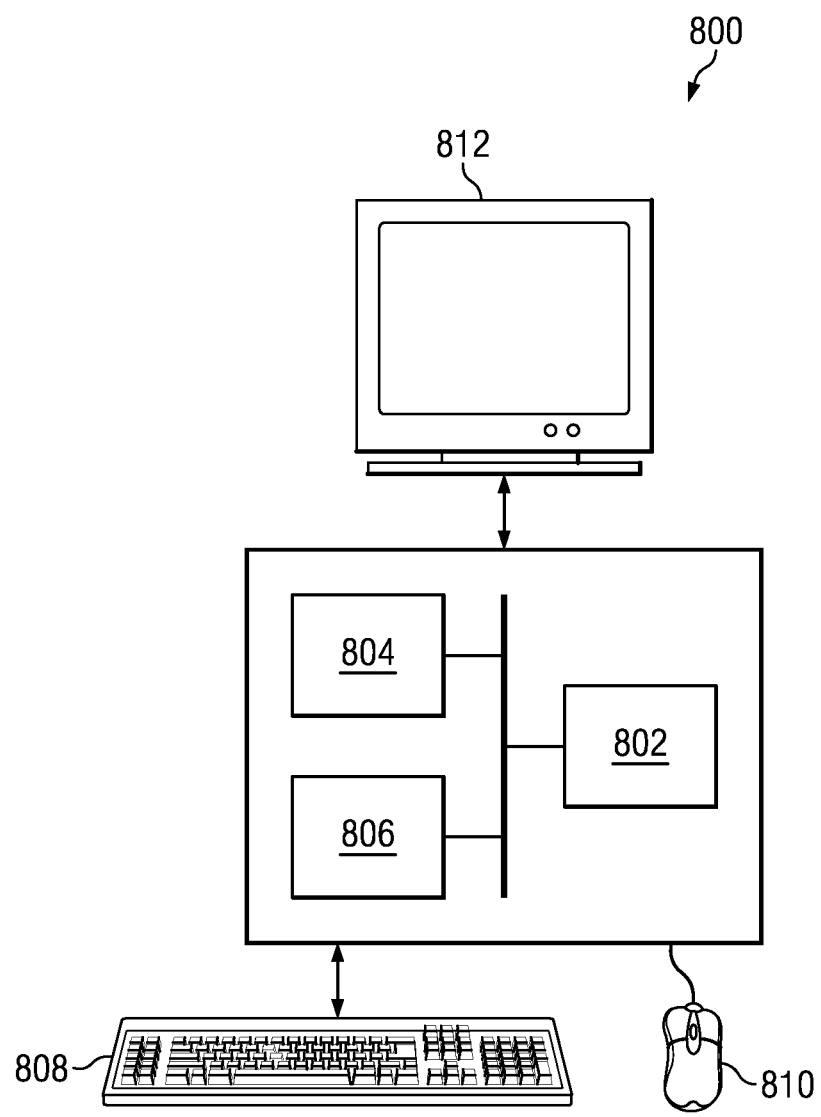
FIG. 8 shows a digital system in accordance with one or more embodiments of the invention.

Embodiments of the methods described herein may be implemented on virtually any type of digital system. For example, as shown in FIG. 8, a digital system (800) includes a processor (802), associated memory (804), a storage device (806), and numerous other elements and functionalities typical of digital systems (not shown). The digital system (800) may also include input means, such as a keyboard (808) and a mouse (810) (or other cursor control device), and output means, such as a monitor (812) (or other display device). The digital system (800) may be connected to a network (not shown) (e.g., a local area network (LAN), a wide area network (WAN) such as the Internet, or any other similar type of network) via a network interface connection (not shown). Those skilled in the art will appreciate that these input and output means may take other forms.

Further, those skilled in the art will appreciate that one or more elements of the aforementioned computer system (800) may be located at a remote location and connected to the other elements over a network. Further, embodiments of the invention may be implemented on a distributed system having a plurality of nodes, where each portion of the system and software instructions may be located on a different node within the distributed system. In one embodiment of the invention, the node may be a computer system. Alternatively, the node may be a processor with associated physical memory. The node may alternatively be a processor with shared memory and/or resources.

Software instructions to perform embodiments of a method as described herein may be stored on a computer readable medium such as a compact disc (CD), a diskette, a tape, a file, memory, or any other computer readable storage device. The software instructions may be distributed to the digital system (800) via removable computer readable media (e.g., floppy disk, optical disk, flash memory, USB key), via a transmission path from computer readable media on another digital system, etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims. It is therefore contemplated that the appended claims will cover any such modifications of the embodiments as fall within the true scope and spirit of the invention.

What is claimed is:

1. A method of digital processor for processing heart monitoring samples, the method comprising:
   computing via the digital processor a folded correlation value for each heart monitoring sample in a plurality of heart monitoring samples, wherein the folded correlation value relates to a portion of Q-wave, R-wave and S-wave and the time reversed version of another portion; and
   identifying and displaying peaks corresponding to heartbeats based on the folded correlation values of the heart monitoring samples.

2. The method of claim 1, further comprising:
   computing a heart rate based on the identified peaks.

3. The method of claim 2, further comprising:
   displaying the heart rate.

4. The method of claim 1, wherein computing a folded correlation value comprises:
   selecting a first frame of N consecutive heart monitoring samples, wherein a first heart monitoring sample in the plurality of heart monitoring samples is a center heart monitoring sample in the first frame, and wherein N is an odd number; and
   computing a folded correlation value for the first heart monitoring sample as a dot product of (N-1)/2 heart monitoring samples preceding the first heart monitoring sample in the first frame and time-reversed (N-1)/2 heart monitoring samples following the first heart monitoring sample in the first frame.

5. The method of claim 4, wherein computing a folded correlation value further comprises:
   selecting a second frame of N consecutive heart monitoring samples, wherein a second heart monitoring sample adjacent to the first heart monitoring sample is a center heart monitoring sample in the second frame; and
   computing a folded correlation value for the second heart monitoring sample as a dot product of (N-1)/2 heart monitoring samples preceding the second heart monitoring sample in the second frame and time-reversed (N-1)/2 heart monitoring samples following the second heart monitoring sample in the second frame.

6. The method of claim 4, wherein N is selected based on one selected from a group consisting of a length of a primary heart sound component S1 and a length of an R-wave.

7. The method of claim 1, further comprising:
   receiving the plurality of heart monitoring samples from one selected from a group consisting of an audio sensor, an accelerometer, and a plurality of electrodes.

8. The method of claim 1, wherein an identified peak is one selected from a group consisting of an R-wave peak or an S1 peak.

9. A method of digital processor for processing heart monitoring samples, the method comprising:
   receiving a monitoring signal comprising the heart monitoring samples;
   dividing via the digital processor the heart monitoring samples into overlapping frames of length N, wherein each frame overlaps a previous frame by N-1 heart monitoring samples and wherein N is an odd number;
   folding heart monitoring samples in each frame around a center heart monitoring sample in the frame to generate a folded correlation value for the center heart monitoring sample, wherein the folded correlation value relates to a portion of Q-wave, R-wave and S-wave and the time reversed version of another portion; and
   identifying and displaying peaks corresponding to heartbeats based on the folded correlation values.

10. The method of claim 9, further comprising:
    computing a heart rate based on the identified peaks.

11. The method of claim 9, wherein folding heart monitoring samples comprises:
    computing a dot product of a first vector consisting of (N-1)/2 heart monitoring samples preceding the center heart monitoring sample in a frame and a second vector consisting of (N-1)/2 heart monitoring samples following the center heart monitoring sample in the frame, wherein the heart monitoring samples in the first vector are in time order and the heart monitoring samples in the second vector are in reverse time order.

12. The method of claim 9, wherein the monitoring signal is received from one selected from a group consisting of an audio sensor, an accelerometer, and a plurality of electrodes.

13. The method of claim 9, wherein an identified peak is one selected from a group consisting of an R-wave peak or an S1 peak.

14. The method of claim 9, wherein N is selected based on one selected from a group consisting of a length of a primary heart sound component S1 and a length of an R-wave.

* * * * *